(12) United States Patent
Jabri

(10) Patent No.: US 7,381,055 B2
(45) Date of Patent: Jun. 3, 2008

(54) DENTAL DEVICES USED FOR FILLING CAVITIES WITH COMPOSITE MATERIAL

(76) Inventor: Saadallah Jabri, 8701 Wedgewood Dr., Burr Ridge, IL (US) 60527

(*) Notice: Subject to any disclaimer, the term of this patent is extended or adjusted under 35 U.S.C. 154(b) by 534 days.

(21) Appl. No.: 10/758,472

(22) Filed: Jan. 15, 2004

(65) Prior Publication Data
US 2005/0158691 A1 Jul. 21, 2005

(51) Int. Cl.
*A61C 7/00* (2006.01)
(52) U.S. Cl. .......... 433/149; 433/39; 433/155
(58) Field of Classification Search .......... 433/37–39, 433/136–138, 148–149, 155
See application file for complete search history.

(56) References Cited

U.S. PATENT DOCUMENTS

| | | | | |
|---|---|---|---|---|
| 2,529,174 A | * | 11/1950 | Muller | 433/155 |
| 4,373,915 A | * | 2/1983 | Comstock | 433/136 |
| 4,718,852 A | * | 1/1988 | Galler | 433/148 |
| 5,460,525 A | * | 10/1995 | Rashid | 433/155 |
| 5,607,302 A | * | 3/1997 | Garrison et al. | 433/39 |
| 5,993,210 A | * | 11/1999 | Godfrey | 433/159 |
| 6,206,697 B1 | * | 3/2001 | Hugo | 433/155 |
| 6,293,796 B1 | * | 9/2001 | Trom et al. | 433/155 |
| 6,325,625 B1 | * | 12/2001 | Meyer | 433/139 |
| 2003/0059741 A1 | * | 3/2003 | Bills | 433/153 |
| 2005/0272005 A1 | * | 12/2005 | Schaffner et al. | 433/149 |

\* cited by examiner

*Primary Examiner*—Ralph A. Lewis
(74) *Attorney, Agent, or Firm*—Miller, Matthias & Hull

(57) ABSTRACT

A dental device for retaining composite material within a cavity is described. The device provides accurate placement of a retaining matrix band which holds dental composite material in place within the cavity under repair and precludes or prevents migration of the dental composite material out of the cavity and down towards the gum line. The disclosed device and methods help to restore the contact area between the two teeth (i.e., the one worked on and the one adjacent to it). An improved mechanical polishing device is also shown and described. Improved methods of repairing cavities with dental composite material using the disclosed devices are also disclosed.

17 Claims, 3 Drawing Sheets

DENTAL DEVICES USED FOR FILLING CAVITIES WITH COMPOSITE MATERIAL

BACKGROUND

1. Technical Field

Dental devices used when filling cavities with composite material are shown and described. More specifically, a matrix band and an installation device for holding the matrix band in place along a tooth are disclosed which assist the dentist in retaining composite filling material in place during the filling of a cavity which is disposed at least partially on a side surface of a molar, i.e., either the mesial, buccal, lingal or distal side of a posterior tooth. The disclosed matrix band and the device for installing the same prevent composite material from migrating downward from the cavity and towards the gum line. Further, an improved mechanical finishing device is also disclosed to facilitate the smoothing or sanding of a composite filling in the proximal areas between the teeth.

2. Background of the Related Art

In modern dentistry, dental composite material is used to fill cavities in teeth in lieu of mercury-containing amalgam. There are two primary reasons for the widespread acceptance of composite materials. First, the composite material is lightly colored, can be tinted to match the corresponding color of the tooth under repair and is therefore more cosmetically appealing than amalgam or gold fillings. Second, the composite material does not contain mercury, and therefore its use is preferred by the consumers regardless of the safety record of amalgam fillings.

After the site of the cavity is drilled, the cavity is washed, dried and treated with primer or etchant. Then, adhesive is applied and then, dental composite, in an uncured state, is applied and driven into or compressed into the prepared cavity site. In an uncured state, the dental composite typically has a paste-like consistency.

After the cavity area has been filled with dental composite, the dental composite is light cured, which causes the dental composite to harden and adhere to the tooth. After curing, the dental composite is polished or shaped to conform to the tooth.

One disadvantage of composite material is associated with its paste-like consistency. Specifically, during the application and filling process, the composite may migrate out of the cavity, down the tooth and penetrate the gum line. The dentist often has to manually remove the composite material that has migrated out of the cavity area and smooth the filling. While matrix bands are available to assist in keeping the composite material in place, dentists have a hard time obtaining or restoring contact between the restored tooth and the adjacent tooth when restoring class II cavities with composite filling because of the thickness of the available matrix bands.

Therefore, there is a need for an apparatus which facilitates the filling of class II cavities with composite material, and, more particularly, an apparatus which facilitates the filling of cavities disposed along a side surface of a molar with composite material without compromising the contact area.

Still another disadvantage associated with the use of composite material is the polishing process after the composite has cured within the filled cavity. Specifically, when the cavity occurs along a side of a molar, and more specifically, along a mesial or distal side of a molar, the dentist has a very difficult time polishing the cured surface. Currently, dentists must manually use a special strip or tape to polish a cured composite disposed along a tooth surface that faces another tooth. This polishing action is cumbersome for the dentist and uncomfortable for the patient. Therefore, there is a need for an improved dental composite polishing apparatus which would make the polishing of cured composite material disposed along a side of a molar easier for both the patient and the dentist.

SUMMARY OF THE DISCLOSURE

In satisfaction of the aforenoted needs, an improved matrix band installation device for retaining composite filling material within a cavity is disclosed which also helps to restore the contact area between the repaired tooth and the adjacent tooth. In an embodiment, the improved matrix band installation device disclosed herein comprises a clamp. The clamp comprises a straddle structure extending traversely between and connecting a pair of generally parallel arms. Each arm comprises a proximal end connected to the straddle and a distal end connected to a wedge. The wedges are connected to the arms and are generally oppositely directed towards each other. The proximal end of the arms are each separately connected to a leg.

The device is used to install a matrix band which comprises a matrix band that comprises two end loops and that is sized so that when each end loop receives one of the legs, the matrix band can be positioned so that the matrix band extends from one of the legs, along one of the arms, around the wedges, along the other arm and to the other leg, with the other loop being received over the other leg.

In practice, the device is inserted into the mouth of the patient so that the wedges are inserted between the tooth to be repaired and an adjacent tooth. The arms extend from the wedges past the tooth to be repaired and towards the straddle. The matrix band, which may be installed with the above-described device, extends from one leg, around the tooth to be filled and to the other leg. A middle portion of the matrix band extends around the prepared cavity and serves as a dam to hold the composite material in place during the filling process. The wedges can act to hold the matrix band in a preferred position. When properly sized and when the band and device are properly installed, the matrix band prevents migration of composite material out from the prepared cavity and downward towards the gum line.

In a refinement, the legs which hold the loops of the matrix band are extensions of the straddle or, alternatively, the legs can be extensions of the arms.

The matrix band may be a polymer material, such as various plastic or polymer materials known to those skilled in the art, or the matrix band may be fabricated from metal, such as various stainless steels. In a further refinement, a middle portion of the matrix band is attached to some cured dental composite material. The dental composite material may be cured to the matrix band thereby providing an effective bond between the composite material and the matrix band or the composite material may be adhered to the matrix band with an adhesive. Other means of adhering the dental composite material to the matrix band will be apparent to those skilled in the art. This composite part of this matrix band extends from the middle of the matrix band and higher than the upper margin of the matrix band. In addition, this composite may eventually become the filling and the matrix band will be removed or separated from the composite when the filling is finished.

In a further refinement, each arm is connected to a tab that provides a gripping surface for engaging a tool for installing and removing the dam from a patient's mouth.

In a refinement, when the matrix band is formed of a metallic material without composite material attached thereto, a lower edge of the metallic band may be slightly thicker than the upper edge. The thicker lower edge of the band is installed in the larger gaps between teeth at or near the gum line while the thinner upper edge of the band is received in the narrower gaps between teeth disposed between the gum line and the chewing surface.

In another refinement, each wedge is tapered and the arms and straddle bias the wedges toward each other so that when the matrix band is installed in the patient's mouth, the wedges can be easily frictionally inserted between the tooth under repair and a neighboring tooth. In a further refinement of this concept, each tab is disposed opposite its respective arm from one of the wedges.

An improved method for repairing a molar is also disclosed which comprises removing a decayed portion of the molar and generally preparing the cavity site for installation for dental composite material, installing the device and matrix band described above in the patient's mouth so that the wedges and matrix band are disposed between the molar under repair and a neighboring tooth with the matrix band disposed along and around a portion of the molar where the decayed portion of the tooth has been removed. The edge will hold the matrix band against the repaired tooth. The method also comprises filling the area of the molar where the decayed portion of the tooth has been removed with composite material and allowing the composite material to engage the matrix band thereby allowing the matrix band to contain the composite material within the molar where the decayed portion of the tooth has been removed, allowing the composite material to cure or set, and removing the matrix band and installation device.

In a refinement of this method, the method also includes polishing between the molar and the neighboring tooth with a mechanical finishing device. The mechanical flossing device may comprise two generally parallel and spaced apart prongs with each prong comprising a proximal end connected to a transmission assembly and a distal end connected to a polishing band that extends between the distal ends of the prongs. The transmission assembly is connected to a shaft. The shaft is connected to a motor or dental drilling apparatus for imparting rotation to the shaft about its longitudinal axis. The transmission assembly comprises an input element connected to the shaft that rotates with the shaft and an output element connected to both prongs. The output element is engagement with the input element so that rotation of the input element results in the output element alternatingly pushing and pulling each prong so that the prongs move in a reciprocatingly forward and backward motion in opposite directions from one another.

In a further refinement of this concept, the input element is a cammed plate connected to an end of the shaft and the output element is a plate in abutting engagement with the cammed plate of the input element.

In an alternative refinement, the input element comprises an input gear connected to the shaft for rotation with the shaft and the output element comprises an output enmeshed with the input gear but which rotates about an axis generally perpendicular to the axis of the shaft. In this embodiment, the output gear is disposed between a connected to two generally oppositely directly arms. Each arm is connected to one of the prongs. In either of these embodiments, the shaft is part of a dental drill assembly.

The mechanical polishing device described above with the above-described method will also be disclosed below separate and apart from the disclosed methods and the disclosed matrix band and installation device.

BRIEF DESCRIPTION OF THE DRAWINGS

The disclosed devices and methods will be described in greater detail below in connection with the following drawings, wherein.

It should be noted that the drawings are not necessarily to scale and that the embodiments are sometimes illustrated with phantom lines, diagrammatic representations and fragmentary views. In certain instances, details which are not necessary for an understanding of the disclosed devices and methods or which render other details difficult to perceive may have been omitted. It should be understood, of course, that this disclosure is not necessarily limited to the particular embodiments illustrated herein.

DETAILED DESCRIPTION OF THE PRESENTLY PREFERRED EMBODIMENTS

Figure 1A:
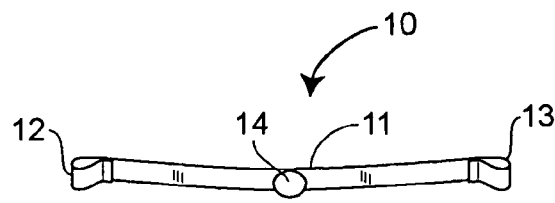
FIG. 1A is a plan view of a matrix band used for containing composite material within a prepared cavity site in accordance with this disclosure.
Figure 1B:
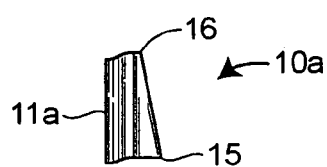
FIG. 1B is a side sectional view of a metallic matrix band having a profile that features a thicker lower edge and a thinner upper edge.
Figure 4:
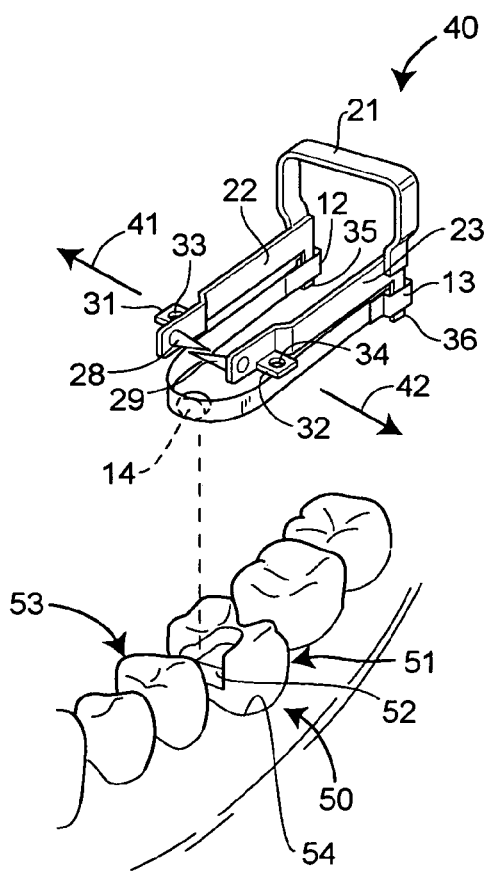
FIG. 4 is a perspective view illustrating the installation of the combination bracket and matrix band of FIG. 3 into a patient's mouth.

In FIG. 1A, a matrix band 10 that is used as a dam for composite material is shown. The matrix band 10 includes a middle section 11 disposed between and connected to two end loops 12, 13. The middle section 11 may be equipped with a portion 14 of dental composite material as shown in FIG. 4 for the reasons explained below. Further, as shown in FIG. 1B a matrix band 10a may be provided with a profile that features a thicker lower end 15 and a thinner upper end 16 with a tapering profile so that the middle portion 11a of the band 10a snugly fits between teeth with the thicker lower edge 15 filling the layer gap between teeth at or near the gum line and the thinner upper edge 16 snugly fitting in the smaller gap between middle portions of two adjacent teeth.

Figure 2:
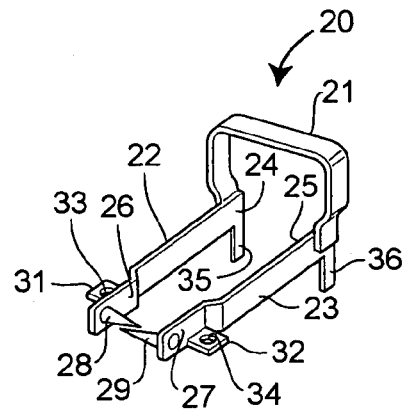
FIG. 2 is a perspective view of a device or clamp for installing and holding the matrix band shown in FIG. 1 in place during the filling of a cavity with composite material.
Figure 5:
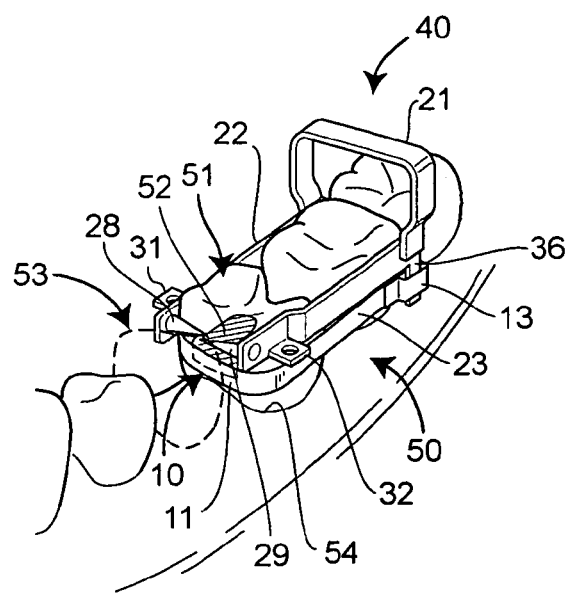
FIG. 5 is a perspective view illustrating the matrix band and bracket device illustrated in FIGS. 1-4 in a patient's mouth.

Turning to FIG. 2, a bracket device 20 for installing the band 10 and holding it in place is disclosed which includes a straddle 21 that extends transversely between two generally parallel arms 22, 23. The arms 22, 23 each include proximal ends 24, 25 that are connected to the straddle 21. Distal ends 26, 27 of the arms 22, 23 are each equipped with inwardly extending wedges 28, 29. The wedges 28, 29 are preferably tapered as shown in FIG. 2. Further, on opposing sides from the wedges 28, 29, the arms 22, 23 are also preferably connected to tabs 31, 32 that provide a gripping surface for an installation tool (not shown). In the embodiment illustrated in FIG. 2, the bracket 20 is preferably installed with a dental tool that includes prongs (not shown) that are accommodated in the holes 33, 34 of the tabs 31, 32 and pressure applied to the tool results in a separation of the arms 22, 23 during installation, and when released, the biasing effect of the straddle 21 would result in the arms 22, 23 and wedges 28, 29 being biased together and secured in the patient's mouth as shown in FIG. 5. The wedges 28, 29 are essentially level with the matrix band 10 is shown in FIG. 5.

Figure 3:
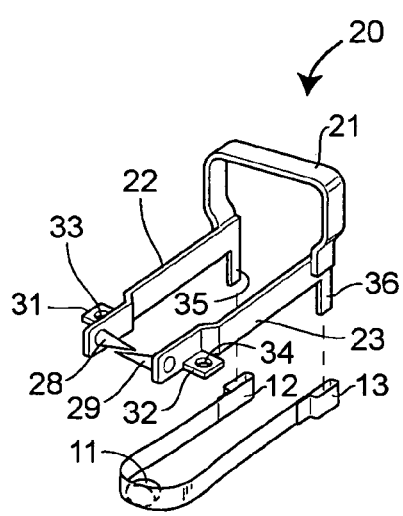
FIG. 3 is a perspective view illustrating the installation of the matrix band of FIG. 1 onto the bracket device of FIG. 2.

Turning to FIGS. 2 and 3, the bracket 20 also includes downwardly extending legs 35, 36 which serve as receiving areas for the loops 12, 13 of the matrix band 10. FIG. 4 illustrates the assembly 40 in place which includes the bracket 20 and matrix band 10 above (or below) a row of molars 50 in a patient's mouth. The dentist would then bias the arms 22, 23 outward away from each in the direction of the arrows 41, 42, using a conventional tool and then lower the assembly 40 in place as shown in FIG. 5. In FIG. 5, the tooth shown at 51 is the tooth under repair and, more specifically, the area shown in phantom at 52 in FIGS. 4-5 is an example of a cavity which has been drilled out and prepared for filling with composite material (not shown).

The assembly 40 is placed in the patient's mouth so that the arms 22, 23 extend along either side of the tooth 51 with the wedges disposed between the tooth 51 under repair and an adjacent tooth 53. The matrix band 10 extends around the tooth 51 and over at least a lower portion of the cavity 52 thereby acting as a dam to prevent migration of composite material out of the cavity 52 and down towards the gum line 54. Upon release of the tabs 31, 32 from the dental tool having prongs received in the holes 33, 34, the arms 22, 23 and wedges 28, 29 are biased inwardly towards each other so that the arms 22, 23 engage the anterior and interior sides of the tooth 51 and so that the wedges 28, 29 are frictionally disposed between the tooth 51 under repair and the neighboring tooth shown at 53. Thus, with the assembly 40 in place as shown in FIG. 5, the matrix band 10 acts as a dam to contain the composite material within the cavity area 52. The assembly 40 therefore prevents the unwanted migration of composite material downward towards the gum line 54 and the pre-cured composite part of the matrix band will obtain or restore the contact area between the two teeth where this pre-cured composite part is going to be part of the filling.

Figure 6:
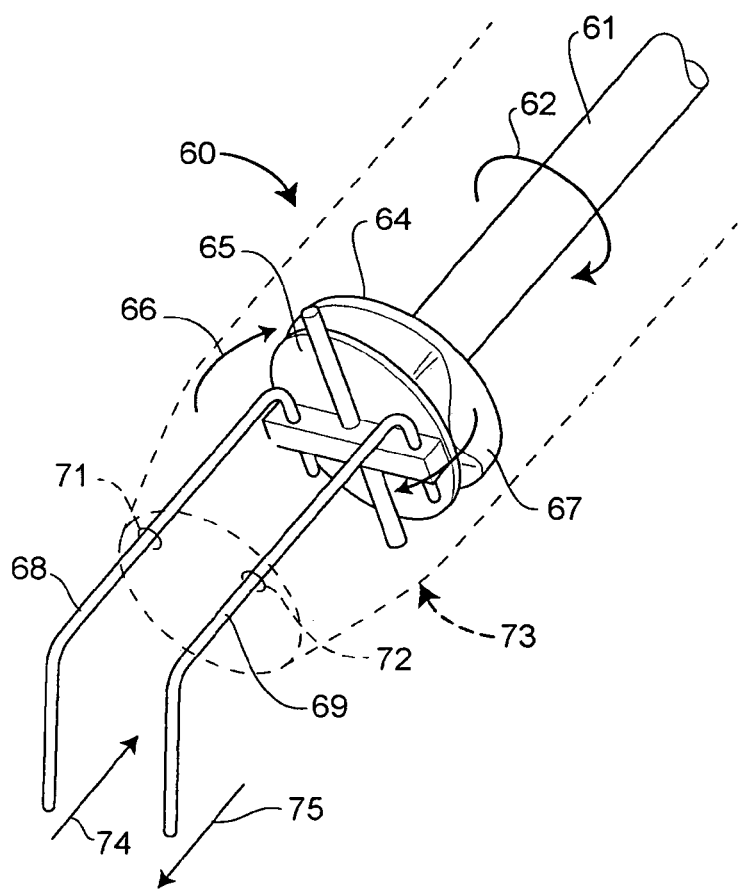
FIG. 6 is a perspective view of a mechanical flossing/finishing/polishing device made in accordance with this disclosure.

Another problem addressed by this disclosure is the finishing or polishing of composite material that has been placed into a cavity 52 and subsequently cured. Specifically, as can be seen in FIG. 4, the polishing of composite material disposed within a cavity 52 disposed on a side of a tooth 51, and substantially between teeth 51, 53 is very problematic. In the past, dentists have had to manually polish this area with a piece of specially designed floss or tape. The polishing procedure is uncomfortable for the patient and cumbersome for the dentist. FIG. 6 illustrates a device 60 that addresses this problem. Specifically, the device 60 includes a shaft 61 that may be connected to a conventional drill assembly for rotation about its longitudinal axis in either direction, but as shown in FIG. 6, in the direction of the arrow 62. Rotation in an opposite direction would also work as well with the device 60 as disclosed. The shaft 61 is connected to a transmission assembly 63 that includes an input member or element 64 connected to an end of the shaft 61. In the embodiment 60 shown in FIG. 6, the input element 64 is a cammed disk.

The transmission assembly 63 also includes an output element or member 65 which, in this case, is plate in abutting engagement with the input element 64. Rotation of the shaft 61 and input element 64 results in a wobbling motion of the output element 65 in a reciprocating manner as shown by the arrows 66, 67. The output element 65 is connected to two generally parallel prong elements 68, 69 that extend outward from holes 71, 72 in the housing shown in phantom at 73. As a result of the wobbling reciprocating motion of the output element 65, the prong elements 68, 69 move in a back and forth and reciprocating motion in opposite directions to each other as indicated by the arrows 74, 75.

Figure 7:
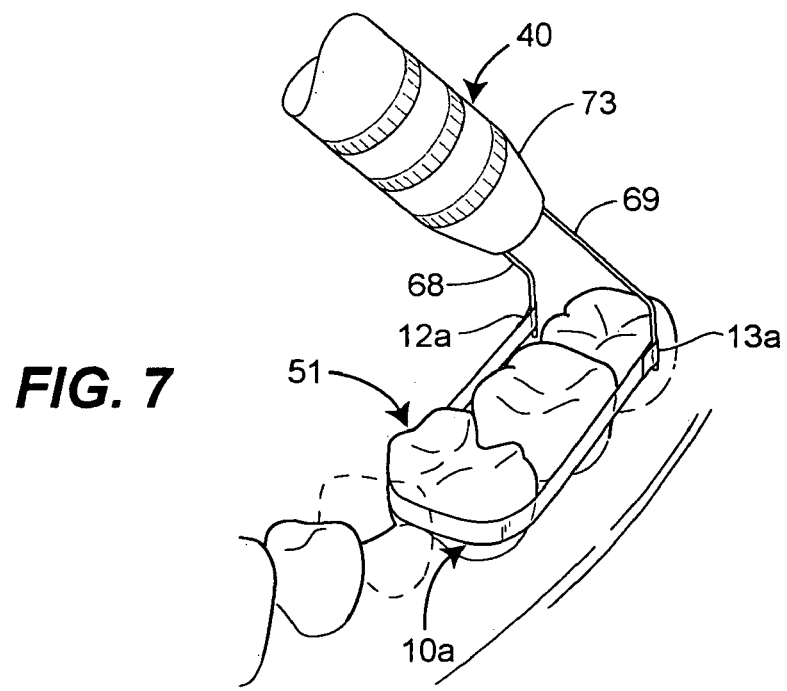
FIG. 7 is a perspective view illustrating the use of the mechanical flossing device illustrated in FIG. 6.

Thus, the rotational movement of the shaft 61 is translated by the transmission element 63 into a reciprocating back and forth motion of the prongs 68, 69 which, as shown in FIG. 7, provides a mechanical flossing device that can be used to polish the repaired side of the molar 51 when the prongs 68, 69 are in inserted through end loops 12a, 13a of a strapped 10a. The matrix band 10a is of a more robust instruction than the matrix band 10 shown in FIG. 1 and used as a dam in FIG. 5. Instead, the flossing/polishing matrix band 10a may have an abrasive quality to it for polishing purposes. The matrix band 10a may need to be stronger than the matrix band 10 used as a dam in FIG. 5.

Figure 8:
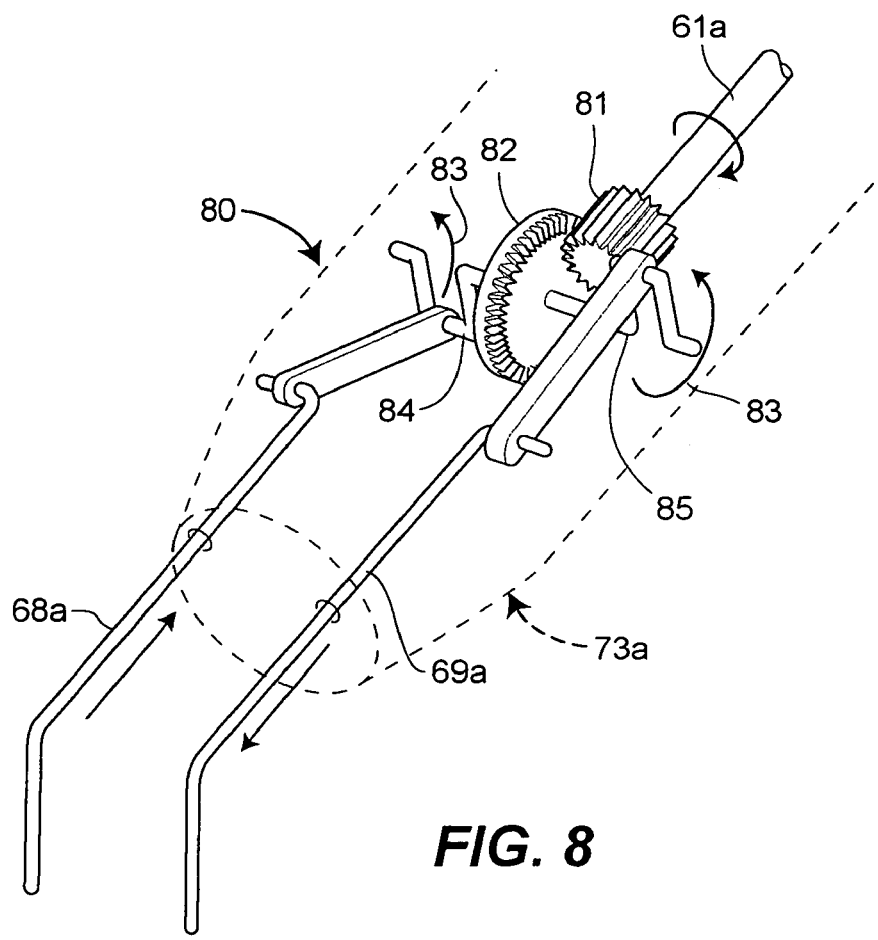
FIG. 8 is an alternative embodiment of the mechanical flossing device shown in FIG. 6.

Turning to FIG. 8, an alternative embodiment 80 is disclosed whereby the shaft 61a is connected to a gear 81. The gear 81 is enmeshed with a disk-shaped gear 82 that rotates about an axis substantially perpendicular to the longitudinal axis of the shaft 61a and gear 81. Rotation of the gear 82 in the direction of the arrows shown at 83 results in rotation of the unshaped arms 84, 85. The arms 84, 85 are generally directed in opposite directions from one another and, in turn, are connected to the prongs elements 68a, 69a as shown. Thus, the rotation of the gear 82 and the direction of the arrows 83 results in the reciprocating and alternating back and forth motion of the prongs 68a, 69a similar to that of the prongs 68, 69 and shown in FIG. 6.

While only certain embodiments have been set forth and described, alternative embodiments and various modifications will be apparent from the above description to those skilled in the art. These and other alternatives are considered equivalents and within the spirit and scope of this disclosure.

What is claimed is:

1. A device for retaining filling material in place during the filling or repair of a cavity, the device comprising:
   a straddle extending traversely between and connecting a pair of generally parallel arms, each arm comprising a proximal end connected to the straddle and a distal end connected to a wedge;
   the wedges connected to the arms being generally oppositely directed towards each other, the proximal ends of the arms each being coupled to the straddle and a downwardly extending leg; and
   a matrix band comprising two end loops, the matrix band being sized so that when each end loop receives one of the legs, the matrix band can be positioned to extend horn one of the legs, below one of the arms, around the wedges, below the other arm and to the other leg.

2. The device of claim 1 wherein the legs are extension of the straddle.

3. The device of claim 1 wherein the legs are generally perpendicular extension of the proximal ends of the arms.

4. The device of claim 1 wherein the matrix band is plastic or metal.

5. The device of claim 1 wherein a middle portion of the matrix hand is attached to a pre-cured dental composite material.

6. The device of claim 1 wherein a middle portion of the matrix band has a profile that includes a lower edge that is thicker than an upper edge with a smooth tapered profile extending therebetween.

7. The device of claim 1 wherein each aim is connected to a tab that provides a gripping surface for engaging a tool for installing and removing the dam from a patient's mouth.

8. The device of claim 7 wherein each tab is disposed opposite its respective arm from one of the wedges.

9. The device of claim 1 wherein each wedge is tapered and the arms and straddle bias the wedges toward each other so that when the dam is installed in a patient's mouth, the wedges can be frictionally inserted between the tooth under repair and a neighboring tooth.

10. The device of claim 1 wherein the straddle has an inverted U-shaped configuration.

11. A method for repairing a molar comprising:
removing a decayed portion of the molar;
installing the device of claim 1 in the patient's mouth so that the wedges and matrix band are disposed between the molar under repair and a neighboring tooth with the matrix band disposed along and around the portion of the molar where the decayed portion has been removed;
filling the area of the molar where the decayed portion has been removed with composite material and allowing the composite material to engage the matrix band and allowing the matrix band to contain the composite material within the molar;
curing the composite material;
removing the dam device.

12. The method of claim 11 wherein the wedges press the matrix band against the tooth to be filled/repaired and these wedges will provide separation o the tooth to be filled and the adjacent tooth.

13. The method of claim 11 further comprising polishing between the molar and neighboring tooth with a mechanical polishing device.

14. The method of claim 13 wherein the mechanical polishing device comprises:
two generally parallel and spaced apart prongs, each prong comprising a proximal end connected to a transmission assembly and a distal end connected to an end of a floss matrix band that extends between the distal ends of the prongs,
the transmission assembly being connected to the shaft, the shaft being connected to a motor for imparting rotation to the shaft about its longitudinal axis,
the transmission assembly comprising an input element connected to the shaft and that rotates with the shaft, the transmission assembly further comprising an output element connected to both prongs and in engagement with the input element so that rotation of the input element results in the output element alternatingly pushing and pulling each prong so that the prongs move reciprocating forward and backward in opposite directions from one another.

15. The method of claim 14 wherein the input element is a cammed plate connected to an end of the shaft and the output element is a plate in abutting engagement with the cammed plate of the input element.

16. The method of claim 14 wherein the input element comprises an input gear' connected to the shaft for rotation with the shaft and the output element comprises an output gear enmeshed with the input gear but which rotates about an axis generally perpendicular to the axis of the shaft, the output gear' being disposed between and connected to two generally oppositely directed arms, each arm being connected to one of the prongs.

17. The method of claim 16 wherein the shaft is part of a dental drill assembly.

* * * * *